(12) United States Patent
Ghelmansarai et al.

(10) Patent No.: US 7,486,983 B2
(45) Date of Patent: Feb. 3, 2009

(54) VERIFICATION OF RADIATION BEAM CHARACTERISTICS

(75) Inventors: Farhad A. Ghelmansarai, Danville, CA (US); Francisco Miguel Hernandez-Guerra, Concord, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1043 days.

(21) Appl. No.: 10/366,203

(22) Filed: Feb. 12, 2003

(65) Prior Publication Data

US 2004/0158145 A1 Aug. 12, 2004

(51) Int. Cl.
*A61N 5/10* (2006.01)

(52) U.S. Cl. .................... 600/427; 378/65; 382/128; 600/407

(58) Field of Classification Search .................... 600/407, 600/427; 378/65; 382/128
See application file for complete search history.

(56) References Cited

U.S. PATENT DOCUMENTS

| 6,148,060 | A | 11/2000 | Collin et al. | |
|---|---|---|---|---|
| 6,350,985 | B1 * | 2/2002 | Rodricks et al. | 250/252.1 |
| 6,626,569 | B2 * | 9/2003 | Reinstein et al. | 378/206 |
| 2002/0021830 | A1 | 2/2002 | Ritt | |

OTHER PUBLICATIONS

Dosimetric Verification of X-Ray Fields With Steep Dose Gradients Using an Electronic Portal Imaging Device, Institute of Physics Publishing, Phys. Med. Biol. 48 (2003) pp. 157-166, S C Vieira, M L P Dirkx, K L Pasma and B J M Heijmen, Published Dec. 23, 2002.

Assessment of Flatness and Symmetry of Megavoltage X-Ray Beam With an Electronic Portal Imaging Device (EPID), G. Liu, T. Van Doorn, and E. Bezak, Dept. of Physics and Mathematical Physics, University of Adelaide, SA, Accepted May 31, 2002.

http://scitation.aip.org/getabs/servlet/GetabsServlet?prog=normal &id=MPHYA6000028000011002..., Medical Physics, Nov. 2001, vol. 28, Issue 11, pp. 2247-2257, Jenghwa Chang, Gikas S. Mageras, Clifton C. Ling and Wendel Lutz, accepted Aug. 17, 2001.

X-ray Quantum Limited Portal Imaging Using Amorphous Silicon Flat-Panel Arrays, P. Munro and D. C. Boulus, accepted for publication Feb. 19, 1998, Med. Phys. 25 (5), May 1998, pp. 689-702.

* cited by examiner

*Primary Examiner*—Ruth S Smith
*Assistant Examiner*—Parikha S Mehta

(57) ABSTRACT

A system to acquire a first image of a radiation field, the radiation field produced by a radiation beam, and to determine a second image based on the first image and based on a reference image of a reference radiation field having substantially homogeneous intensity, the second image representing characteristics of the radiation beam. Some embodiments provide acquisition of a first profile associated with a radiation beam using a radiation detection device, acquisition of a first image of a first radiation field produced by the radiation beam using an imaging device, determination of a map between the first image and the first profile, acquisition a second image of a second radiation field using the imaging device, and determination of a second profile based on the map and the second image.

12 Claims, 16 Drawing Sheets

VERIFICATION OF RADIATION BEAM CHARACTERISTICS

BACKGROUND

1. Field

The present invention relates generally to radiation therapy, and more particularly to calibrating and/or verification systems used in conjunction with such therapy.

2. Description

According to conventional radiation therapy, a radiation beam is directed toward a tumor located within a patient. The radiation beam delivers a predetermined dose of therapeutic radiation to the tumor according to an established therapy plan. The delivered radiation kills cells of the tumor by causing ionizations within the cells.

Radiation therapy plans are designed to maximize radiation delivered to a target while minimizing radiation delivered to healthy tissue. These goals may not be achieved if the radiation is not delivered exactly as required by the therapy plan. More specifically, errors in radiation delivery can result in low irradiation of tumors and high irradiation of sensitive healthy tissue. The potential for mis-irradiation increases with increased delivery errors.

Radiation may be incorrectly delivered if characteristics of the radiation beam do not match beam characteristics on which the plan is based. In this regard, a radiation therapy plan is designed in view of expected characteristics of the radiation beam that will be used to deliver the therapeutic radiation. These characteristics include particular values of flatness, symmetry and penumbra. Other parameters on which a plan may be based include the divergence of the radiation beam, the distance over which the beam will travel to the therapy area, and attenuative properties of organs and other internal patient structures surrounding the therapy area.

FIG. 1a shows a profile of a radiation field produced by a radiation beam. The field comprises the intersection of the radiation beam with a plane such as a surface of a radiation imaging device. Profile 1 represents variations in the intensity of the radiation field over a central axis of the radiation field. Profile 1 may be used to determine the flatness of the radiation beam. In one example, the flatness is defined as a percentage equal to $|(I_{max}-I_{min})/(I_{max}+I_{min})|*100$.

Profile 1 may also be used to determine the penumbra of the beam. The left penumbra and the right penumbra may be defined, respectively, as the distance between the 80% intensity level and the 20% intensity level on the left and right sides of the central axis. As shown, the intensity level at the center of the central axis is normalized to 100%.

The values of profile 1 shown in FIG. 1b may be used to determine a symmetry of the radiation beam. The symmetry may also be expressed as a percentage. According to some systems, the symmetry is equal to $[(A_1+A_2+\ldots A_n)/n-(B_1+B_2+\ldots B_n)/n]/[(A_1+A_2+\ldots A_n)/n-(B_1+B_2+\ldots B_n)/n]/2*100$.

Since a therapy plan may be based on expected values of beam characteristics, these characteristics are often verified prior to delivering radiation according to the plan. Conventional verification systems use a scanning ion chamber to receive a radiation beam and to record intensities at various points of a radiation field produced by the beam. The beam characteristics are computed based on the intensities as described above and verified against expected values. Such systems can be cumbersome, time-consuming and/or otherwise inefficient.

Other beam verification systems acquire an image of the radiation field using a conventional imaging device and determine the intensities at various points of the field based on the image. However, variations in the determined intensities may result from both variations in the beam and differences in the sensitivities of the imaging elements of the imaging device. Accordingly, beam characteristics that are determined based on the intensities do not reliably reflect actual characteristics of the beam.

It would therefore be beneficial to provide a system that may offer more efficient and accurate determination of beam characteristics.

SUMMARY

To address at least the above problems, some embodiments provide a system, method, medium, apparatus, and means to acquire a first image of a radiation field, the radiation field produced by a radiation beam, and to determine a second image based on the first image and based on a reference image of a reference radiation field having substantially homogeneous intensity, the second image representing characteristics of the radiation beam. According to some embodiments, the determination includes correction of the first image for differences in pixel sensitivities, wherein the differences in pixel sensitivities are represented by the reference image.

In some embodiments, a first profile associated with a radiation beam is acquired using a radiation detection device, a first image of a first radiation field produced by the radiation beam is acquired using an imaging device, a map between the first image and the first profile is determined, a second image of a second radiation field is acquired using the imaging device, and a second profile is determined based on the map and the second image.

The claimed invention is not limited to the disclosed embodiments, however, as those skilled in the art can readily adapt the teachings herein to create other embodiments and applications.

BRIEF DESCRIPTION OF THE DRAWINGS

The exact nature of the claimed invention, as well as its objects and advantages, will become readily apparent from consideration of the following specification as illustrated in the accompanying drawings, in which like reference numerals designate like parts, and wherein:

DETAILED DESCRIPTION

The following description is provided to enable any person skilled in the art to make and use the claimed invention and sets forth the best mode contemplated by the inventors for carrying out the claimed invention. Various modifications, however, will remain readily apparent to those in the art.

Figure 1A:
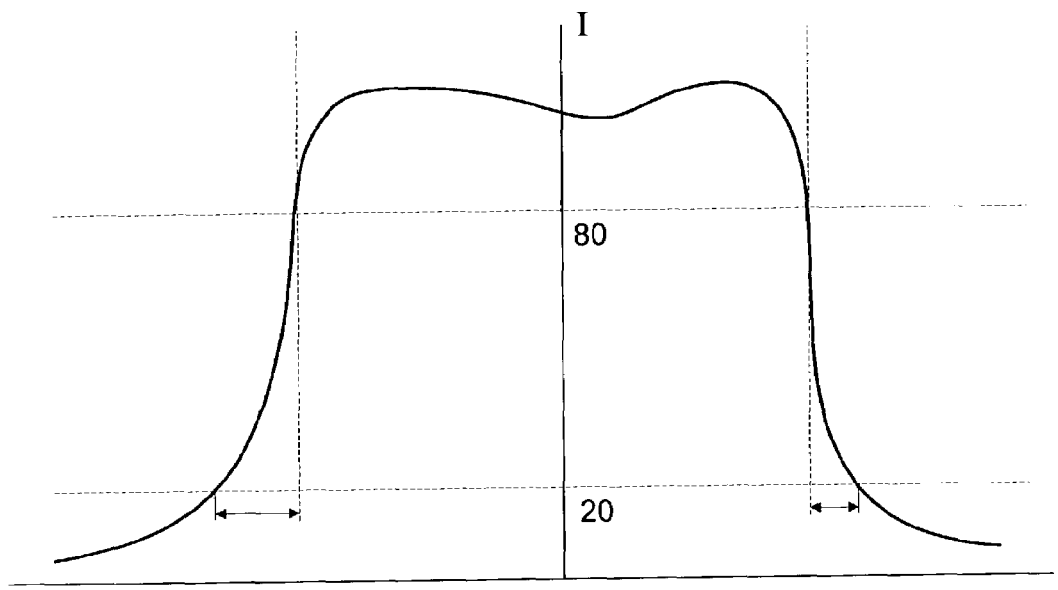
FIG. 1a illustrates beam profile values used to calculate beam flatness and beam penumbra.
Figure 1B:
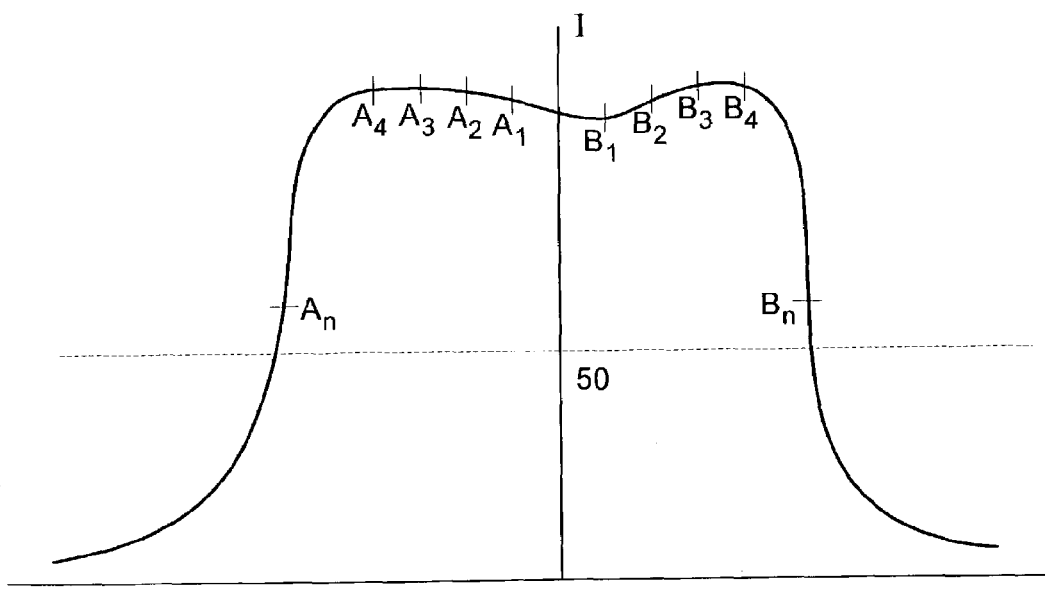
FIG. 1b illustrates beam profile values used to calculate beam symmetry.
Figure 2:
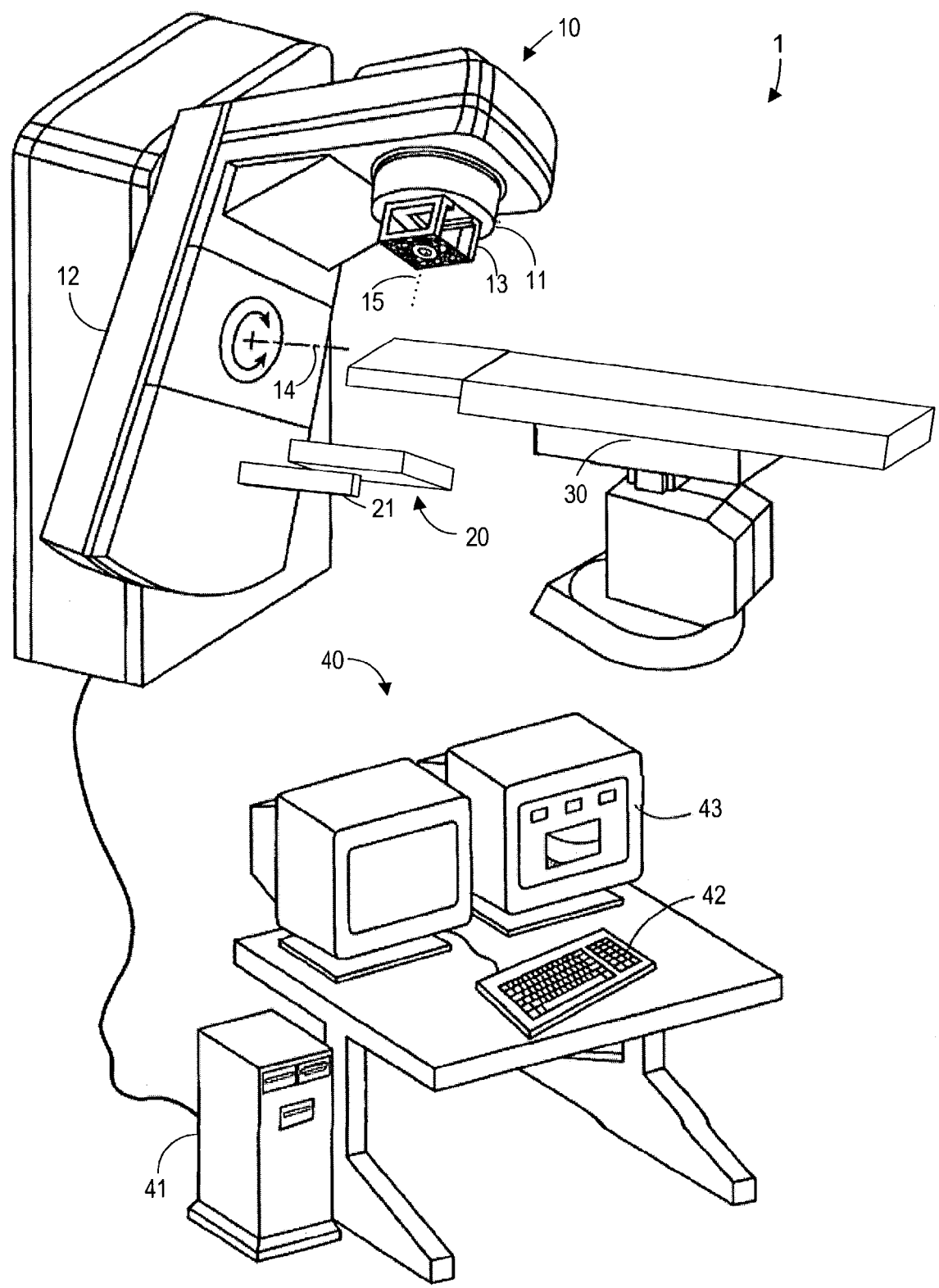
FIG. 2 is a view of a radiation therapy room.

FIG. 2 illustrates radiation therapy room 1 pursuant to some embodiments. Radiation therapy room 1 includes linear accelerator (linac) 10, imaging device 20, table 30 and operator station 40. The elements of radiation therapy room 1 are used to deliver therapeutic radiation to a patient according to a radiation therapy plan.

Linac 10 generates and emits the therapeutic radiation, and is primarily composed of treatment head 11 and gantry 12. Treatment head 11 includes a beam-emitting device (not shown) for emitting a radiation beam used during calibration, verification, and/or treatment. The radiation beam may comprise electron, photon or any other type of radiation. Also included within treatment head 11 is a beam-shielding device, or collimator (not shown) for shaping the beam and for shielding sensitive surfaces from the beam.

Accessory tray 13 is mounted on treatment head 11 and may be configured to receive and securely hold attachments used during the course of treatment planning and treatment. These attachments may include reticles, wedges, or the like for further defining field sizes and intensities.

Treatment head 11 is fastened to a projection of gantry 12. Gantry 12 is rotatable around gantry axis 14 before, during and after radiation treatment. During such treatment, radiation is delivered from linac 10 to the beam-emitting device of treatment head 11 and is emitted therefrom as a beam having axis 15. The beam is emitted towards a point, known as the isocenter, which is located at the intersection of axis 15 and gantry axis 14. Due to divergence of the radiation beam and the shaping of the beam by the aforementioned beam-shaping devices, the beam delivers radiation to a radiation field rather than only to the isocenter.

Imaging device 20 acquires images that are used before, during and after radiation therapy. For example, imaging device 20 is used to acquire images for verification and recordation of a patient position and of an internal patient portal to which radiation is delivered. Images acquired by imaging device 20 may also be used according to some embodiments of the invention to determine characteristics of a radiation beam emitted from linac 10. As described above, the effectiveness of radiation therapy often depends on the characteristics of the radiation beam. Some embodiments to determine beam characteristics using imaging device 20 are set forth in detail below.

In some embodiments, imaging device 20 is a flat-panel imaging device using a scintillator layer and solid-state amorphous silicon photodiodes deployed in a two-dimensional array. The RID1640, offered by Perkin-Elmer®, Inc. of Fremont, Calif., is one suitable device. Imaging device 20 may be attached to gantry 12 in any manner, including via extendible and retractable arm structure 21.

In operation, the scintillator layer receives x-rays and generates light in proportion to the intensity of the received x-rays. The array of photodiodes receives the light and records the intensity of received light as stored electrical charge. The stored charge therefore comprises an acquired image that represents intensities at each location of a radiation field produced by a radiation beam. The bounds of the radiation field are determined by the physical intersection of the radiation beam with the surface of the scintillator layer.

Imaging device 20 may comprise other types of imaging devices. For example, X-ray radiation may also be converted to and stored as electrical charge without use of a scintillator layer. In such imaging devices, x-rays are absorbed directly by an array of amorphous selenium photoconductors. The photoconductors convert the x-rays directly to stored electrical charge that comprises an acquired image of a radiation field. Imaging device 20 may also comprise a CCD or tube-based camera. Such an imaging device may include a light-proof housing 21 within which are disposed a scintillator, a mirror, and a camera.

Table 30 supports a patient during radiation therapy. Table 30 is adjustable to ensure, along with rotation of gantry 12, that a therapy area of the patient is positioned at the isocenter. Table 30 may also be used to support devices used for calibration and/or verification.

Operator station 40 includes a processor 41 in communication with an input device such as keyboard 42 and an operator console 43 (including one or more visual display units or monitors). Operator station 40 is typically operated by an operator who administers actual delivery of radiation therapy as prescribed by an oncologist. Operator station 40 may be located apart from linac 10, such as in a different room, in order to protect the operator from radiation. For example, linac 10 may be located in a heavily shielded room, such as a concrete vault, which shields the operator from radiation generated by linac 10.

The operator uses keyboard 42 to perform calibration and/or verification procedures. These procedures may include verification of beam characteristics, radiation and light field congruence, and field shape, as well as acquisition of data used for image correction. Operator console 43 displays data to the operator before, during and after therapy.

Processor 41 may store processor-executable process steps according to some embodiments of the present invention. In some aspects, the process steps are executed by processor 41, linac 10, imaging device 20, and/or another device to acquire a first image of a radiation field, the radiation field produced by a radiation beam, and to determine a second image based on the first image and based on a reference image of a reference radiation field having substantially homogeneous intensity, the second image representing characteristics of the radiation beam. According to some embodiments, the determination includes correction of the first image for differences in pixel sensitivities, wherein the differences in pixel sensitivities are represented by the reference image.

In some embodiments of the process steps, a first profile associated with a radiation beam is acquired using a radiation detection device, a first image of a first radiation field produced by the radiation beam is acquired using an imaging device, a map between the first image and the first profile is determined, a second image of a second radiation field is acquired using the imaging device, and a second profile is determined based on the map and the second image.

The process steps may be stored by any medium, including a fixed disk, a floppy disk, a CD-ROM, a DVD-ROM, a Zip™ disk, a magnetic tape, or a signal. Some or all of the process steps may also be stored in one or more devices. Moreover, some or all of the foregoing process steps may be implemented in hardware, such as a hardware card installed in processor 41 and discrete circuitry of imaging device 20.

Of course, each of the devices shown in FIG. 2 may include less or more elements than those shown. In addition, embodiments are not limited to the devices shown in FIG. 2.

Figure 3:
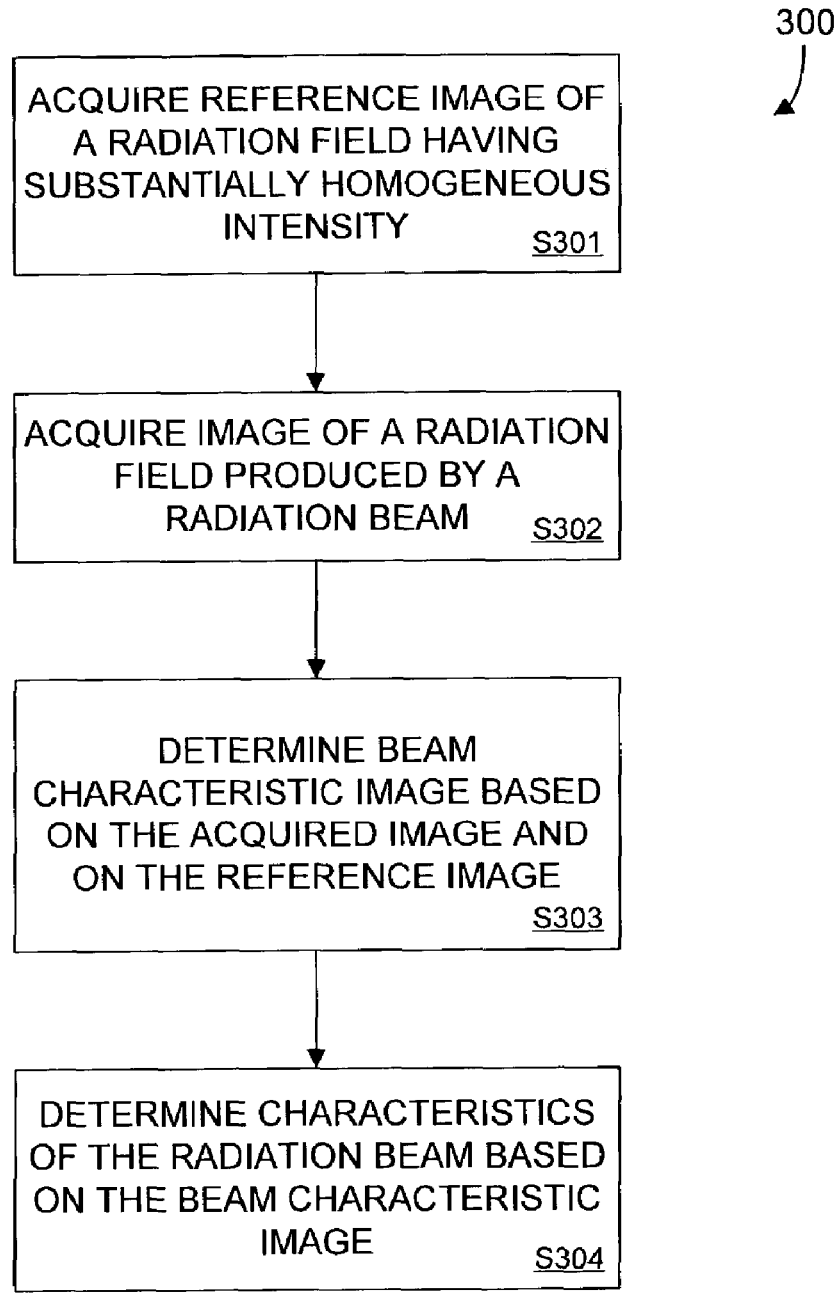
FIG. 3 is a flow diagram of process steps according to some embodiments.

FIG. 3 is a flow diagram of process steps 300 according to some embodiments. Process steps 300 may be embodied, in whole or in part, by hardware of and/or software executed by devices including but not limited to processor 41, linac 10, and imaging device 20.

A reference image is initially acquired in step S301. The reference image is an image of a radiation field having substantially homogeneous intensity. The radiation field may be produced by a radiation beam emitted from any radiation source.

Figure 4:
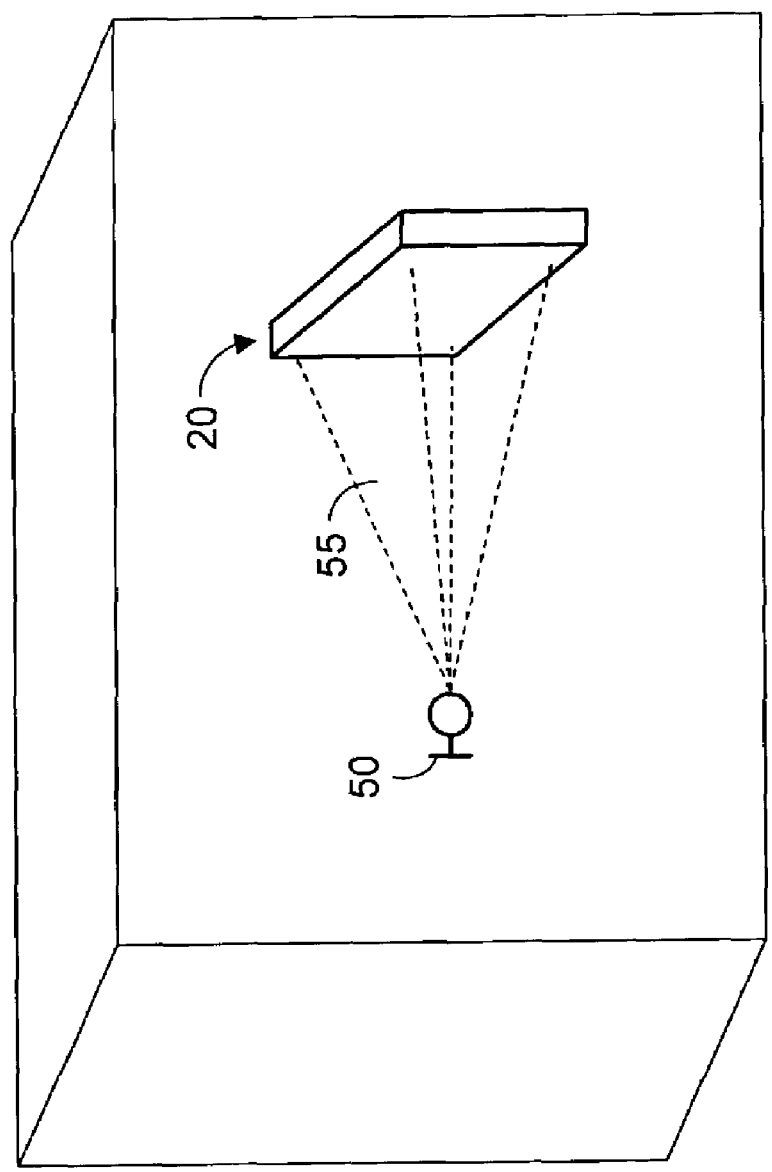
FIG. 4 illustrates acquisition of a reference image according to some embodiments.

FIG. 4 illustrates acquisition of a reference image according to some embodiments of step S301. FIG. 4 shows radiation source 50 emitting radiation beam 55 toward imaging device 20. Radiation beam 55 may comprise any type of radiation, including visible light, electron radiation, and x-ray radiation. As described above, the radiation field produced by radiation beam 55 on the surface of imaging device 20 has substantially homogeneous intensity. Suitable implementations of radiation source 50 may include a Cobalt-60 radiation source.

The radiation field need not be substantially homogeneous at every point on the surface of imaging device 20, but may rather be substantially homogeneous only within a field area of interest. The dimensions of the field area of interest may correspond to a size of a radiation field to be acquired by imaging device 20 during subsequent radiation therapy.

In a case that beam 55 comprises visible light, a scintillator screen of imaging device 20 is removed therefrom prior to step S301. Since a scintillator screen of imaging device 20 may be sealed within a housing of imaging device 20 during manufacture, step S301 may be performed during manufacture of imaging device 20 and before the screen is sealed within the housing. Step S301 may also be performed in radiation therapy room 1 prior to radiation therapy. The scintillator screen, if any, is used during step S301 in a case that beam 55 comprises x-ray radiation.

Figure 5:
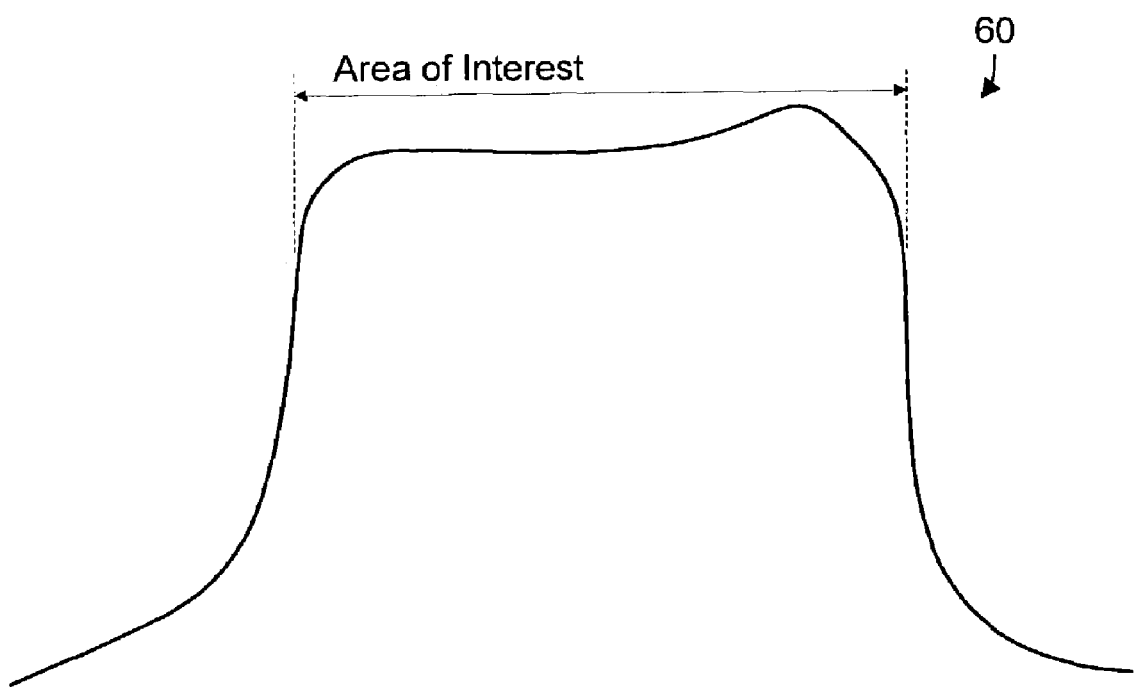
FIG. 5 illustrates a reference image according to some embodiments.

FIG. 5 illustrates reference image 60 acquired in step S301. For simplicity, reference image 60 reflects the intensity of the radiation field over one row or column of imaging device 20. The reference image acquired in step S301 may reflect the intensity of the radiation field over more than one row and/or column of imaging device 20. Since the radiation field produced by radiation beam 55 is substantially homogeneous, variations in the intensities shown in image 60 within the field of interest are due substantially to differences in the sensitivities of corresponding pixels of imaging device 20.

Next, an image of a radiation field produced by a radiation beam is acquired in step S302. The radiation beam may be emitted from linac 10 toward imaging device 20 as shown in FIG. 2. As described above, the radiation field is defined by the intersection of the radiation beam with the surface of imaging device 20. The radiation beam may comprise a beam of therapeutic radiation to be delivered according to a therapy plan. Step S302 may therefore occur during beam verification procedures that occur prior to radiation therapy.

Figure 6:
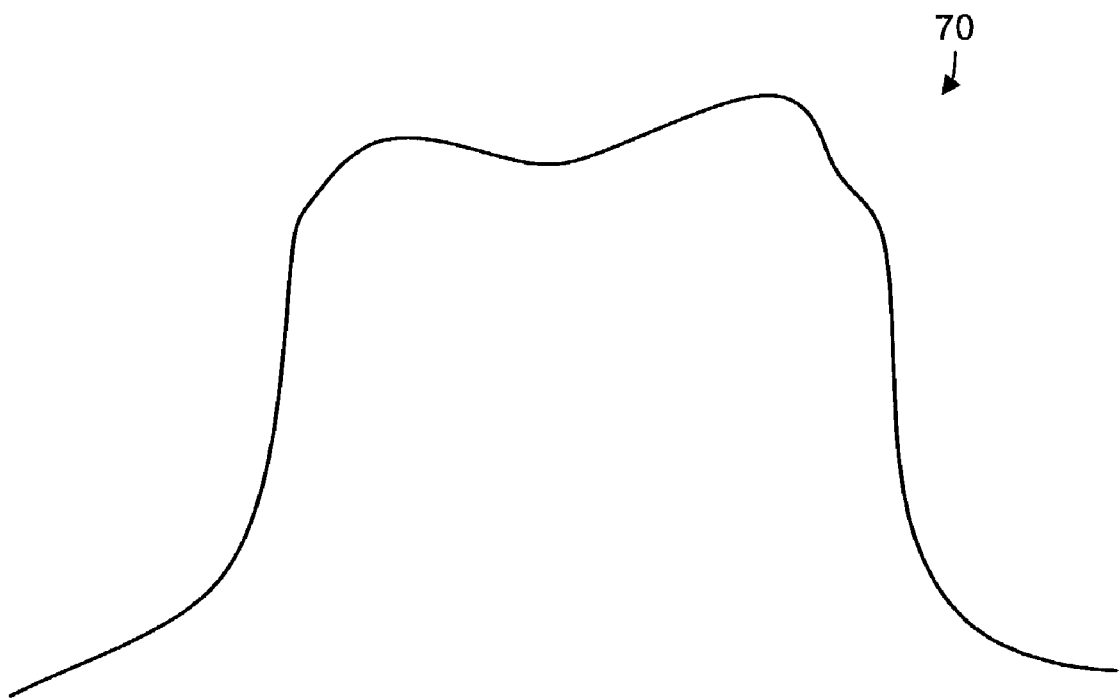
FIG. 6 illustrates a first image of a radiation field according to some embodiments.

FIG. 6 shows image 70 as acquired in step S302. Image 70 reflects the intensity of the radiation field over one row or column of imaging device 20. In some embodiments, the one row or column is identical to the one row or column associated with reference image 60. Image 70 therefore reflects both variations in intensities of the radiation field and differences in the sensitivities of the pixels of imaging device 20 over the one row or column.

A beam characteristic image is determined in step S303. The beam characteristic image is determined based on the reference image and on the image acquired in step S302. In some embodiments of step S303, the image acquired in step S302 is corrected for differences in pixel sensitivities as represented in the reference image. Accordingly, the reference image may be used as a gain correction image so as to normalize the acquired image in view of the differences in pixel sensitivities. More particularly, intensity values of the acquired image are reduced for those pixels having a greater-than-average sensitivity and are increased for those pixels having a less-than-average sensitivity.

Figure 7:
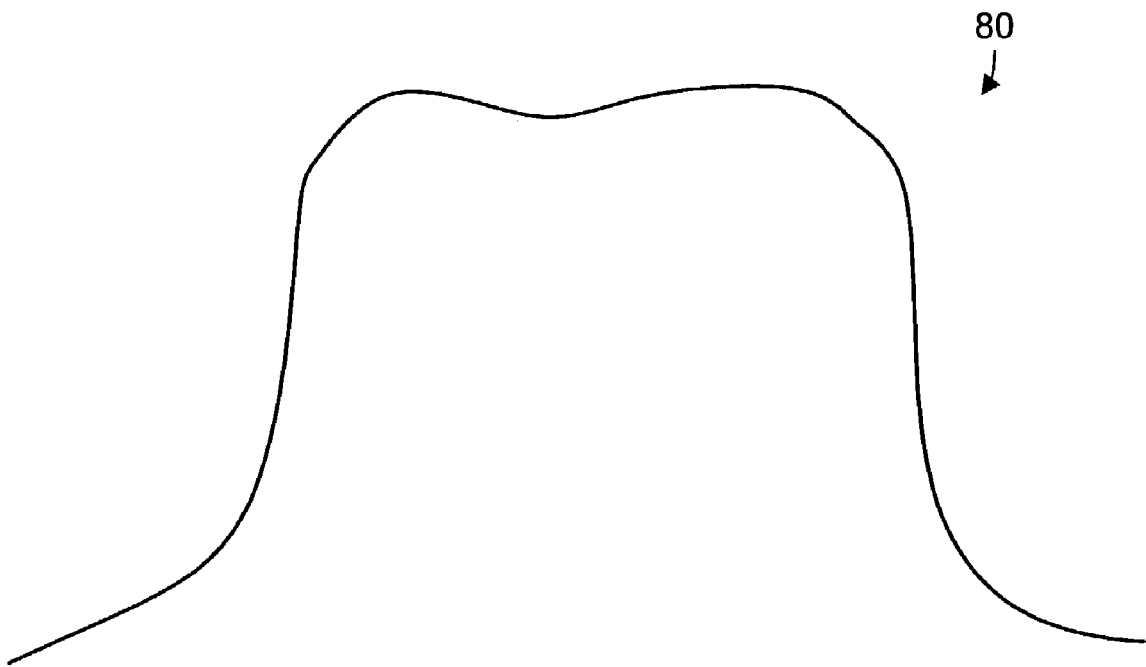
FIG. 7 illustrates a second image determined based on the reference image and on the first image according to some embodiments.

Beam characteristic image 80 of FIG. 7 is determined based on reference image 60 and image 70. As described above, reference image 60 represents differences in pixel sensitivities over one row or column of imaging device 20 and image 70 represents both variations in intensities of the radiation field and differences in the sensitivities of the pixels over the row or column. Since reference image 60 is used as a gain correction image, beam characteristic image 80 represents substantially only the variations in intensities of the radiation field. As a result, beam characteristic image may be used to reliably determine characteristics of the radiation beam emitted from linac 10.

Characteristics of the radiation beam are therefore determined in step S304 based on the beam characteristic image. The determined characteristics may include one or more of beam flatness, beam symmetry, beam penumbra, and other characteristics. The characteristics may be determined using the techniques described in the foregoing Background.

In some embodiments of process steps 300, a water equivalent build-up is placed at the isocenter of linac 10 during step S302. As a result, the image acquired in step S302 reflects any attenuation, scattering, or other distortion of the radiation beam caused by the water equivalent build-up. Such an arrangement may be used in order to produce a beam characteristic image that is comparable to beam characteristic images that are conventionally produced using scanning ion chambers. In this regard, the scanning ion chambers are often immersed in a water equivalent build-up. According to some conventions, the water equivalent build-up is 5 cm thick for radiation energies less than 6 MeV and 10 cm thick for radiation energies equal to or greater than 6 MeV.

Figure 8A:
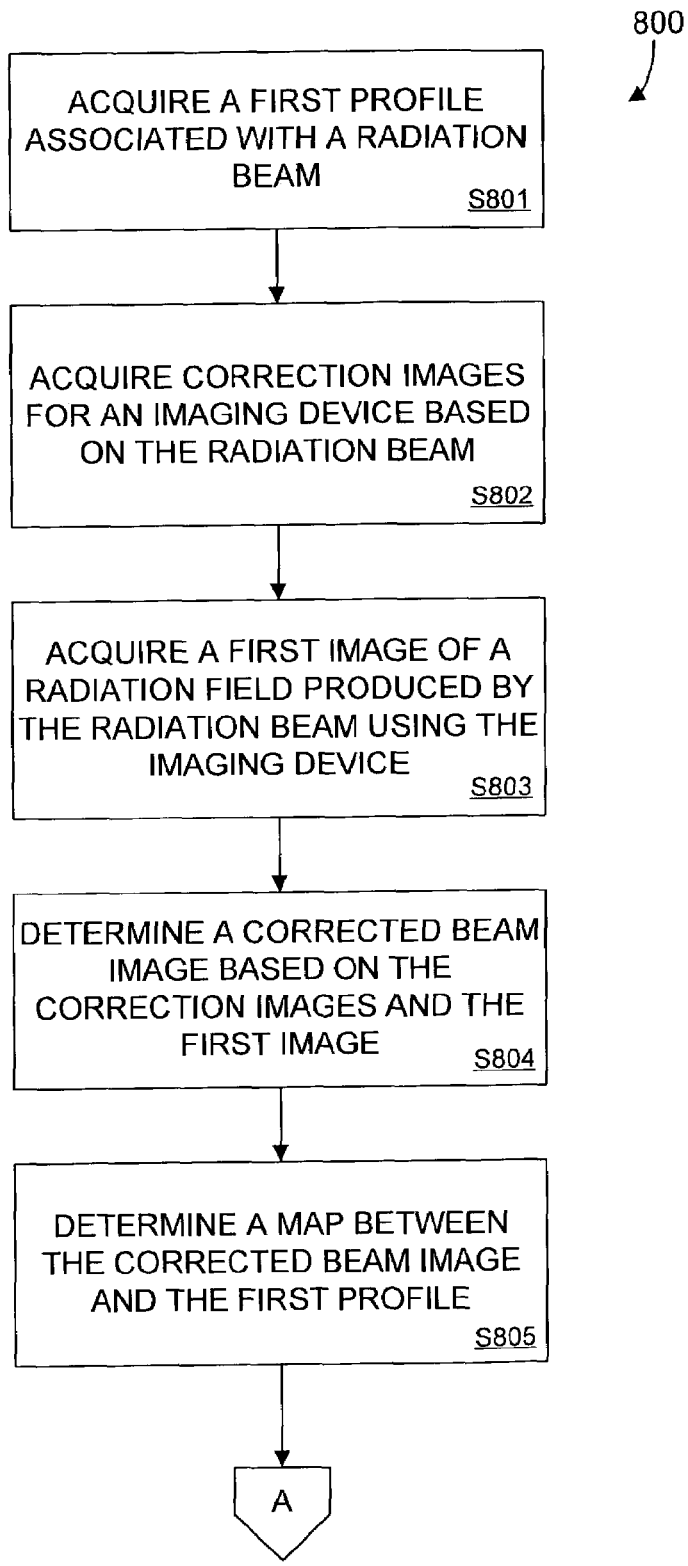
FIGS. 8a and 8b comprise a flow diagram of process steps according to some embodiments.
Figure 8B:
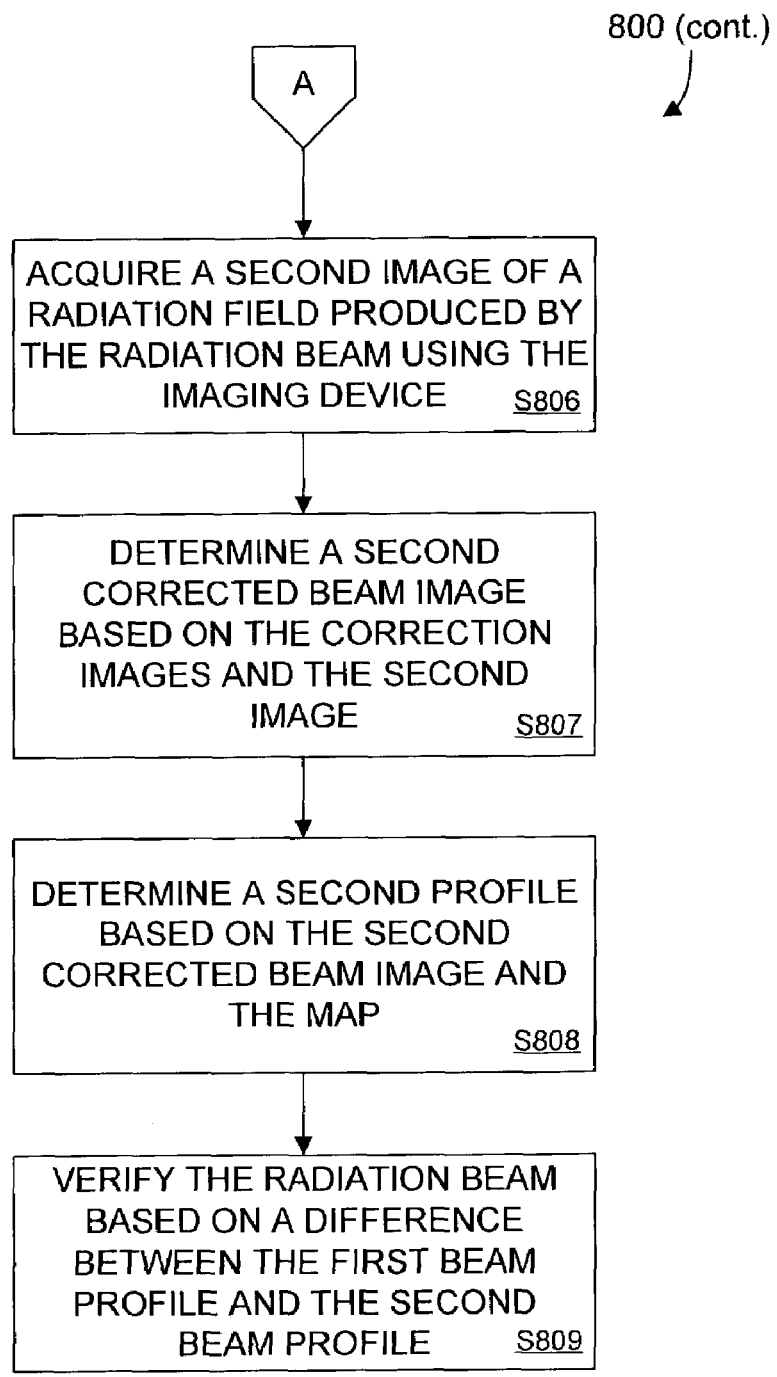

FIGS. 8a and 8b comprise a flow diagram of process steps 800 according to some embodiments. Process steps 800 may be embodied, in whole or in part, by hardware of and/or software executed by devices including but not limited to processor 41, linac 10, and imaging device 20.

Figure 9:
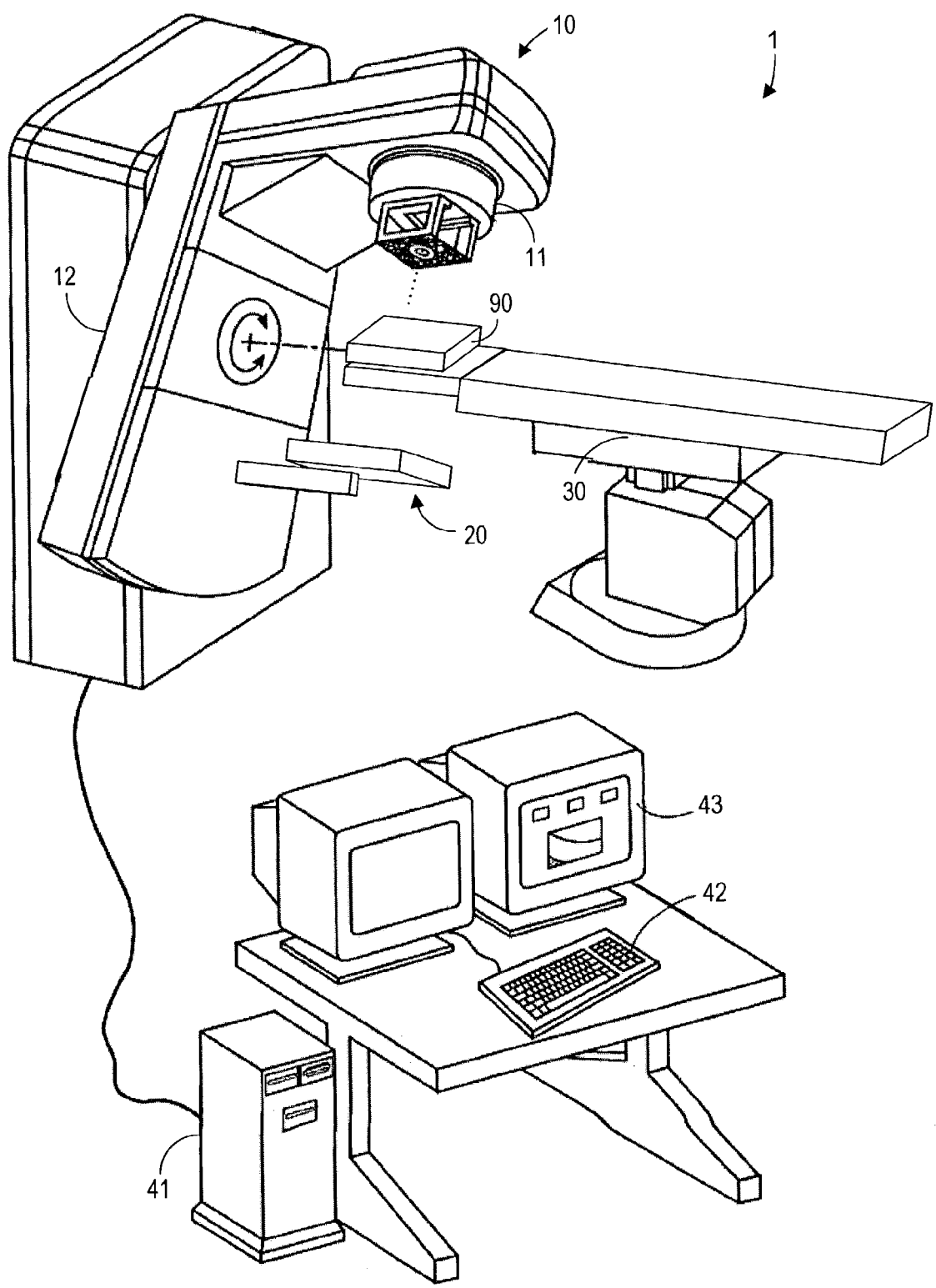
FIG. 9 is a view of a radiation therapy room.

Process steps begin at step S801, in which a first profile associated with a radiation beam is acquired. The first profile may be acquired using a radiation detection device such as a scanning ion chamber. FIG. 9 illustrates radiation therapy room 1 during step S801 according to some embodiments. As shown, scanning ion chamber 90 is placed on table 30 between treatment head 11 and imaging device 20. Scanning ion chamber 90 may comprise a water phantom having a depth of 10 cm and in which are disposed radiation detectors such as thermoluminescent detectors or the like.

Figure 10:
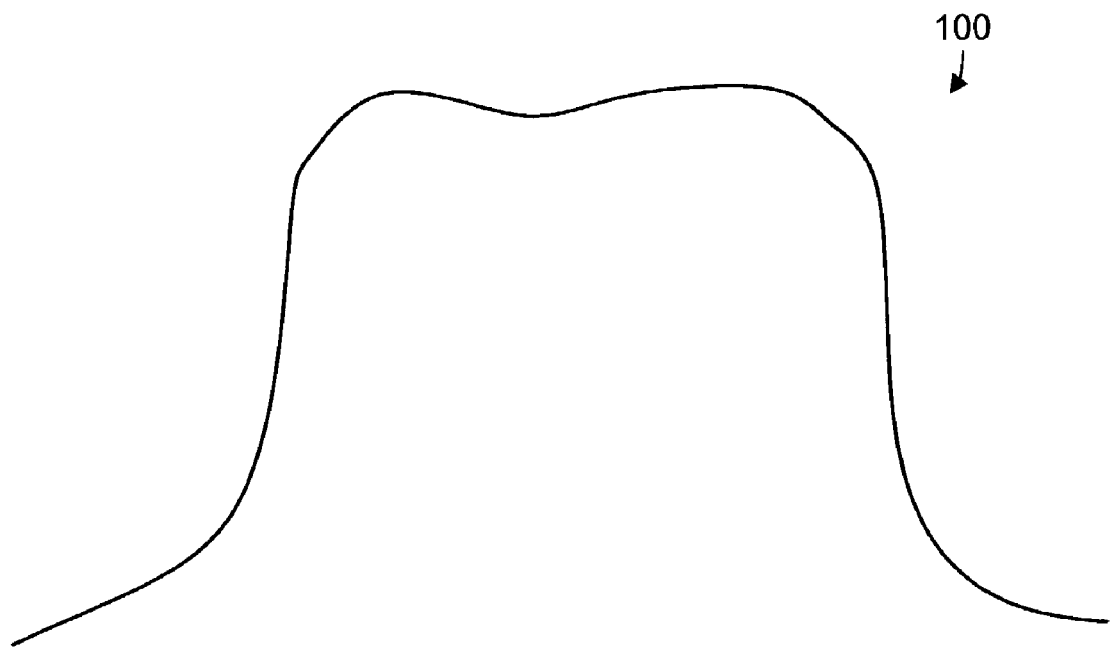
FIG. 10 illustrates a beam profile.

Although gantry 12 is rotated to provide a view of treatment head 11, gantry 12 may be positioned during step S801 such that a radiation beam emitted from treatment head 11 is normal to an upper surface of scanning ion chamber 90. A profile of the emitted beam is acquired by scanning ion chamber 90 and processor 41. FIG. 10 illustrates a profile of a radiation beam according to some embodiments. Profile 100 represents radiation intensities at several locations along a major axis of a radiation field produced by the radiation beam. The profile acquired in step S801 may represent radiation intensities at any points of the radiation field, and may represent the radiation intensities in any graphical, tabular or other manner.

Step S801 may be performed monthly, weekly, or at other intervals to acquire a reference profile of a radiation beam to be used for radiation therapy. The acquired reference profile may be used to design radiation therapy plans.

Correction images are acquired for imaging device 20 based on the radiation beam in step S802. The correction images may be acquired anytime before radiation therapy, but are commonly acquired in the early morning prior to the administration of radiation therapy throughout the day. In some embodiments, the acquired correction images include images used for offset correction, gain correction, and dead pixel correction.

Many imaging devices that convert radiation to electrical charge require biasing of their imaging elements. This biasing generates a small "dark current" that may cause a charge to accumulate within an imaging element that is unrelated to the intensity of radiation received by the imaging element. This dark current thereby causes errors in the calculated intensity of a radiation field location that is associated with the image pixel.

Offset correction is intended to remove the effects of dark current from acquired images. Images are acquired during a period of non-irradiation, and an average image is calculated from the acquired frames. The average image is used to "offset correct" subsequently-acquired images as will be described below with respect to step S804. The averaged images are preferably acquired at a same rate as the subsequently-acquired images so as to better approximate the effect of dark current on the subsequently-acquired frames. Since the extent of dark current effects may vary across imaging devices, imaging devices are often sold with customized software for performing offset correction.

A gain correction image is also acquired in step S802 by irradiating imaging device 20 with the radiation beam while no object lies between the radiation source and imaging device 20. The gain correction image therefore represents both differences in sensitivity and gain among pixels of imaging device 20 and differences in intensities of a radiation field produced by the radiation beam. The gain correction image is also used to identify non-functioning pixels of imaging device 20, or "dead" pixels. An image, or map, is generated based on the identified dead pixels and the map is used to reassign the value of each dead pixel to a value that is based on values of neighboring pixels.

Next, in step S803, a first image of a radiation field produced by the radiation beam is acquired. The radiation field comprises the intersection of the radiation beam with the imaging elements of imaging device 20 while conditions existing during step S801 between the source of the radiation beam and imaging device 20 are simulated. For example, in a case that scanning ion chamber 90 used in step S801 comprises a 10 cm water build-up, a 10 cm water build-up is placed at a same position during step S803.

Figure 11:
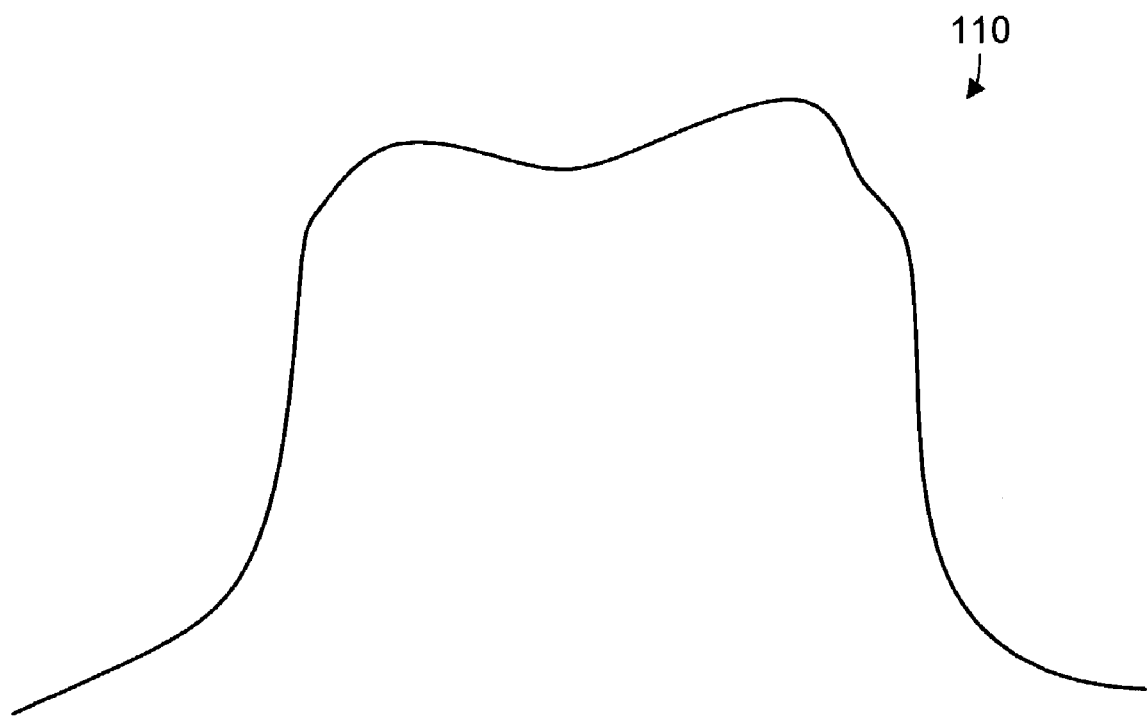
FIG. 11 comprises an image acquired by an imaging device according to some embodiments.

FIG. 11 illustrates the first image acquired in step S803. Image 110 reflects characteristics of the radiation beam as well as differences in the sensitivities of pixels of imaging device 20 over one row or column of imaging device 20. The one row or column may correspond to the axis represented by profile 100.

A corrected beam image is determined in step S804 based on the correction images and on the first image acquired in step S803. In some embodiments, step S804 consists of using the correction images to correct the first image. For example, the pixel intensities represented in the offset image are subtracted from corresponding pixel intensities of the first image. The gain correction image is used to remove intensity variations due to differences in pixel sensitivities of imaging device and differences in radiation intensities of the radiation field produced by the radiation beam. The dead pixel map is then used to generate intensity values for inoperative imaging elements of imaging device 20.

Figure 12:
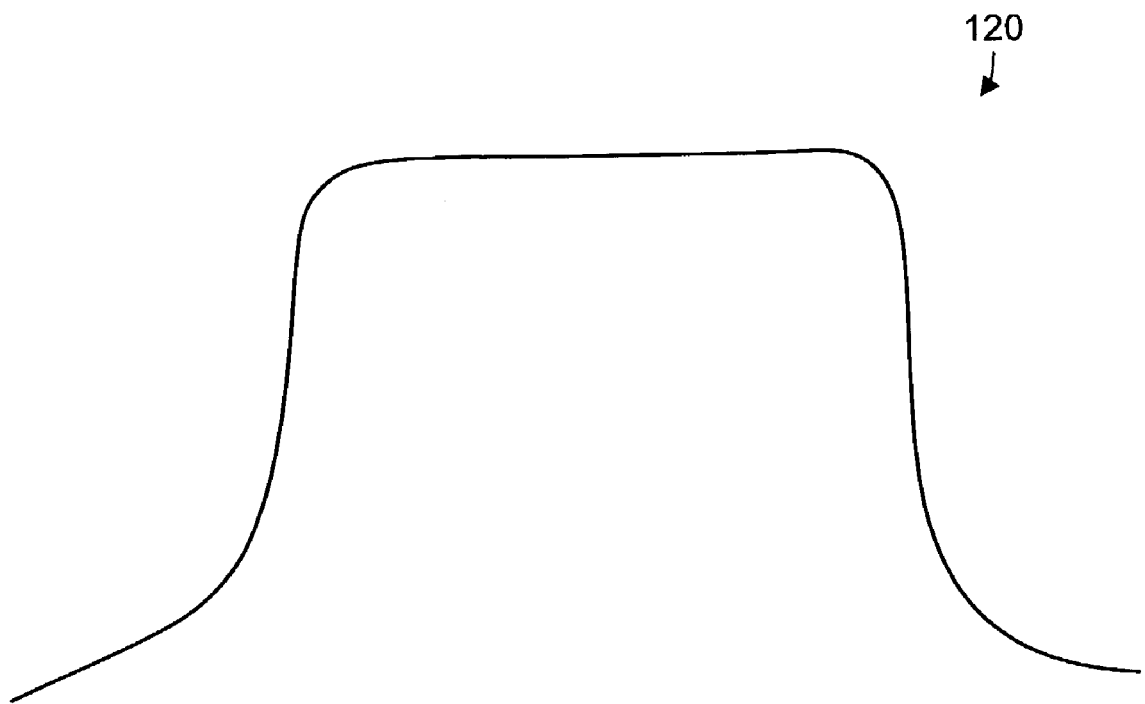
FIG. 12 comprises a corrected image according to some embodiments.

FIG. 12 illustrates corrected beam image 120 according to some embodiments. As shown, corrected beam image 120 represents a radiation field having no intensity variations within an area of interest.

Next, in step S805, a map that translates pixel values between the first profile and the corrected beam image is determined. In some embodiments, the map consists of values associated with each pixel of corrected beam image 120. The value associated with a particular pixel is equal to a difference between the intensity of the pixel in first profile 100 and the intensity of the pixel in corrected beam image 120. Other mapping techniques may also or alternatively be used in step S805.

Figure 13:
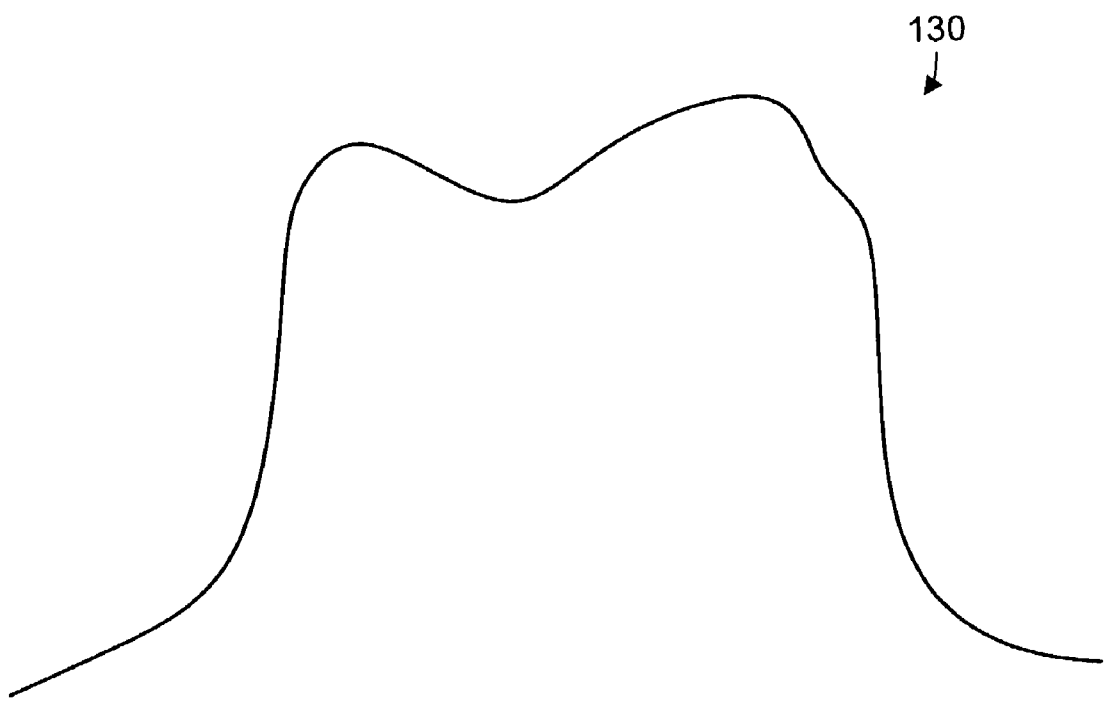
FIG. 13 comprises an image acquired by an imaging device according to some embodiments.

The map may be used to determine changes in the characteristics of the radiation beam. In this regard, a second image of a second radiation field produced by the radiation beam is acquired using imaging device 20 in step S806. The second image may be acquired as described above with respect to step S803. FIG. 13 illustrates second image 130 of a second radiation field as acquired according to some embodiments of step S806.

Figure 14:
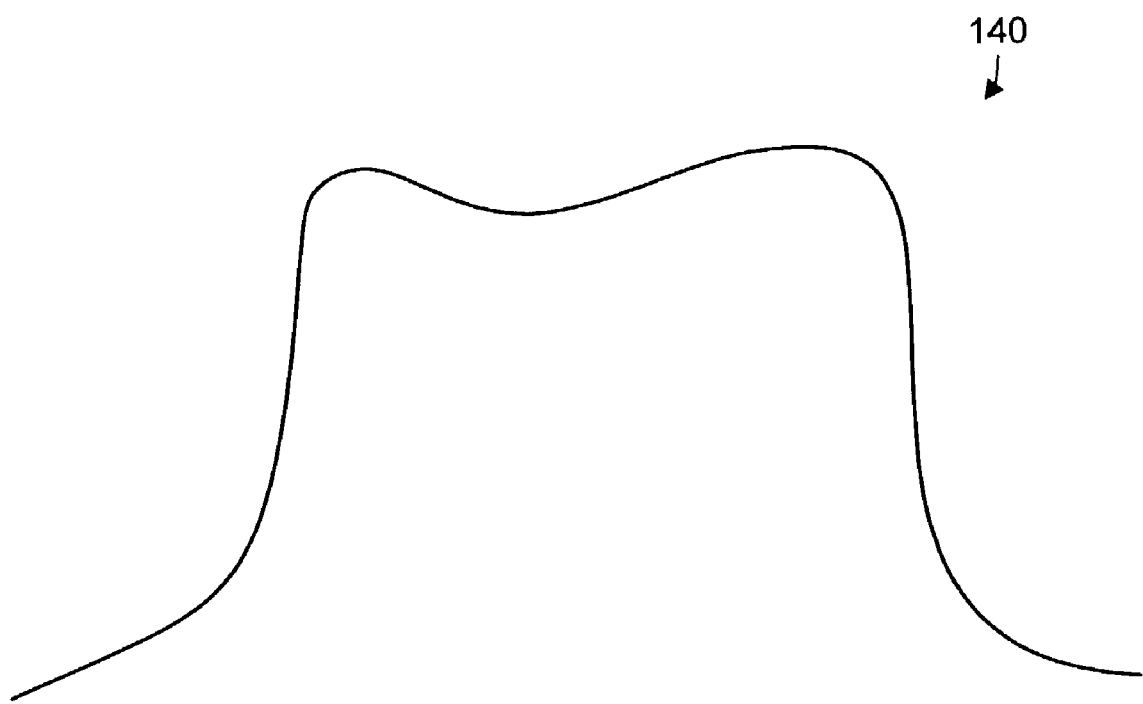
FIG. 14 comprises a corrected image according to some embodiments.

Then, as described with respect to step S804, a second corrected beam image is determined in step S807 based on the correction images and on the second image. Such a corrected beam image is illustrated as image 140 of FIG. 14. Image 140 differs from image 120 of FIG. 12 due to differences in the intensities represented in image 130 and image 110.

Figure 15:
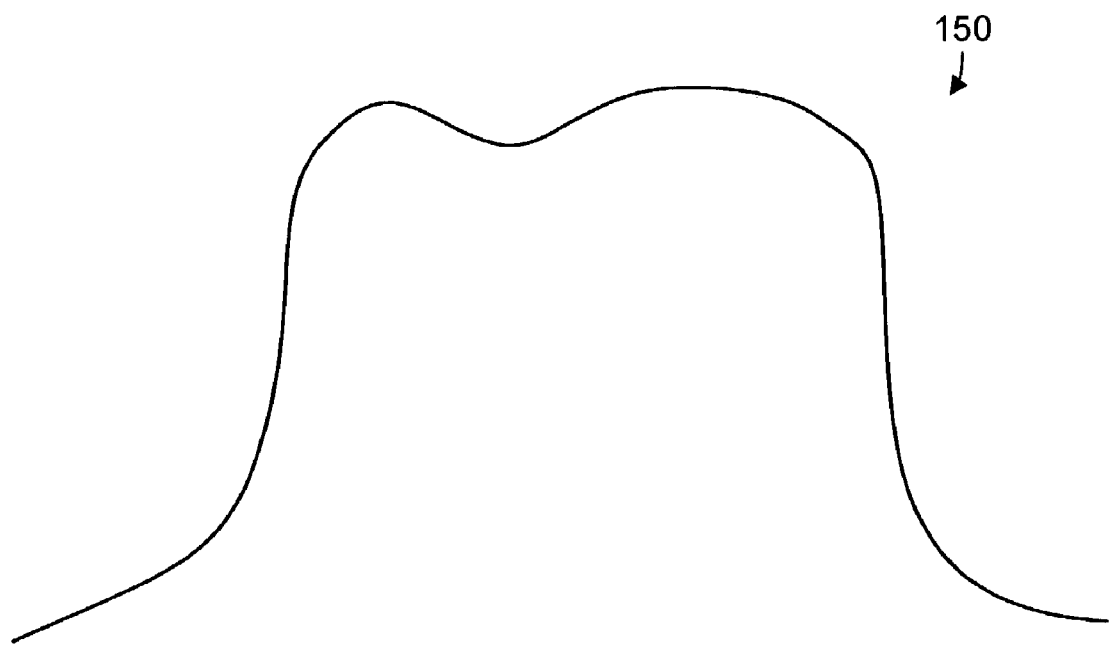
FIG. 15 comprises a beam profile according to some embodiments.

A second profile is determined in step S808 based on the second corrected beam image and on the map determined in step S805. In some embodiments, the map associates a value with each pixel in the area of interest. For each pixel of the second corrected beam image, the value associated with the pixel by the map is added to the value of the pixel in the image. FIG. 15 shows second profile 150, which was determined in step S808 based on image 140 and on the map between image 120 and first profile 100. Second profile 150 differs from first profile 100 due to the differences between image 140 and image 120.

Next, in step S809, the radiation beam is verified based on differences between the first beam profile and the second beam profile. Some embodiments of step S809 include determining a difference between the first profile and the second profile, and determining whether the second radiation field is within a specified tolerance of the first radiation field of step S803 based on the difference. Any currently- or hereafter-known system may be used to determine a difference between the first profile and the second profile. For example, curve-matching algorithms may be used to determine a quantitative difference between the first profile and the second profile.

Steps S806 through S809 may be performed days or weeks after step S805 in order to determine whether characteristics of the radiation beam differ from the characteristics of the beam as represented in the first profile. This verification may be particularly useful prior to delivery of therapeutic radiation according to a therapy plan that was designed in view of the first profile.

Those in the art will appreciate that various adaptations and modifications of the above-described embodiments can be configured without departing from the scope and spirit of the claimed invention. Also, some embodiments differ from the above description. For example, some embodiments of process steps 800 do not include steps S802, S804 and S807. According to some of these embodiments, the map is determined between the first image and the first profile in step S805.

Therefore, it is to be understood that, within the scope of the appended claims, the claimed invention may be practiced other than as specifically described herein.

What is claimed is:

1. A method comprising:
    acquiring a first profile associated with a radiation beam using a scanning ion chamber;
    acquiring a first image of a first radiation field produced by the radiation beam using an imaging device;
    determining a map between the first image and the first profile;
    acquiring a second image of a second radiation field using the imaging device; and
    determining a second profile based on the map and the second image.

2. A method according to claim 1, further comprising:
    determining a difference between the first profile and the second profile.

3. A method according to claim 2, further comprising:
    determining that the second radiation field is within a specified tolerance of the first radiation field based on the difference.

4. A medium storing processor-executable process steps, the process steps comprising:
    a step to acquire a first profile associated with a radiation beam using a scanning ion chamber;
    a step to acquire a first image of a first radiation field produced by the radiation beam using an imaging device;
    a step to determine a map between the first image and the first profile;
    a step to acquire a second image of a second radiation field using the imaging device; and
    a step to determine a second profile based on the map and the second image.

5. A medium according to claim 4, the process steps further comprising:
    a step to determine a difference between the first profile and the second profile.

6. A medium according to claim 5, the process steps further comprising:
    a step to determine that the second radiation field is within a specified tolerance of the first radiation field based on the difference.

7. A device comprising:
    a memory storing processor-executable process steps;
    a processor in communication with the memory and operative in conjunction with the stored process steps to:
        acquire a first profile associated with a radiation beam using a scanning ion chamber;
        acquire a first image of a first radiation field produced by the radiation beam using an imaging device;
        determine a map between the first image and the first profile;
        acquire a second image of a second radiation field using the imaging device; and
        determine a second profile based on the map and the second image.

8. A device according to claim 7, the processor further operative in conjunction with the stored process steps to:
    determine a difference between the first profile and the second profile.

9. A device according to claim 8, the processor further operative in conjunction with the stored process steps to:
    determine that the second radiation field is within a specified tolerance of the first radiation field based on the difference.

10. A system comprising:
    a linear accelerator configured to emit a radiation beam;
    a scanning ion chamber configured to acquire a first profile associated with the radiation beam;
    an imaging device configured to acquire a first image of a first radiation field produced by the radiation beam, and to acquire a second image of a second radiation field; and
    a processor configured to determine a map between the first image and the first profile, and to determine a second profile based on the map and the second image.

11. A system according to claim 10, the processor further configured to determine a difference between the first profile and the second profile.

12. A device according to claim 11, the processor further configured to determine that the second radiation field is within a specified tolerance of the first radiation field based on the difference.

* * * * *